United States Patent
Eversull et al.

(10) Patent No.: US 11,191,935 B2
(45) Date of Patent: Dec. 7, 2021

(54) IMPLANT DELIVERY SYSTEM WITH HYDRATION PROMOTOR CAPABILITY

(71) Applicant: NANO PRECISION MEDICAL, INC., Emeryville, CA (US)

(72) Inventors: Christian S. Eversull, Emeryville, CA (US); Stephen A. Leeflang, Emeryville, CA (US); William G. M. Fischer, Emeryville, CA (US); Wouter E. Roorda, Emeryville, CA (US)

(73) Assignee: NANO PRECISION MEDICAL, INC., Emeryville, CA (US)

( * ) Notice: Subject to any disclaimer, the term of this patent is extended or adjusted under 35 U.S.C. 154(b) by 282 days.

(21) Appl. No.: 16/365,492

(22) Filed: Mar. 26, 2019

(65) Prior Publication Data
US 2019/0217070 A1    Jul. 18, 2019

Related U.S. Application Data

(63) Continuation of application No. PCT/US2017/054897, filed on Oct. 3, 2017.

(60) Provisional application No. 62/404,027, filed on Oct. 4, 2016.

(51) Int. Cl.
| | |
|---|---|
| *A61M 31/00* | (2006.01) |
| *A61K 9/00* | (2006.01) |
| *A61M 37/00* | (2006.01) |
| *A61J 3/00* | (2006.01) |
| *A61M 39/02* | (2006.01) |

(52) U.S. Cl.
CPC ............ *A61M 31/002* (2013.01); *A61J 3/00* (2013.01); *A61K 9/0024* (2013.01); *A61M 31/007* (2013.01); *A61M 37/0069* (2013.01); *A61M 39/0208* (2013.01); *A61M 2039/0205* (2013.01)

(58) Field of Classification Search
CPC ............ A61M 31/002; A61M 39/0208; A61M 31/007; A61M 37/0069; A61M 2039/0205; A61K 9/0024
See application file for complete search history.

(56) References Cited

U.S. PATENT DOCUMENTS

| | | |
|---|---|---|
| 7,687,431 B2 | 3/2010 | Nakayama et al. |
| 9,511,212 B2 | 12/2016 | Roorda |
| 9,770,412 B2 | 9/2017 | Mendelsohn et al. |
| 9,814,867 B2 | 11/2017 | Mendelsohn et al. |
| 10,045,943 B2 | 8/2018 | Roorda |

(Continued)

FOREIGN PATENT DOCUMENTS

| | | |
|---|---|---|
| WO | WO 2006/023315 A2 | 3/2006 |
| WO | WO 2016/123027 A1 | 8/2016 |

OTHER PUBLICATIONS

European Patent Office; International Search Report dated Jan. 19, 2018 for PCT/US2017/054897—2 pgs.

*Primary Examiner* — Bradley J Osinski
(74) *Attorney, Agent, or Firm* — Kilpatrick Townsend & Townsend LLP

(57) ABSTRACT

The invention pertains to apparatuses, means and methods to promote uptake of biocompatible fluids into a reservoir of an implantable drug delivery system though a porous membrane. Embodiments of the invention promote fluid uptake by creating a pressure differential between the reservoir of the drug delivery device and the biocompatible fluid outside the device.

16 Claims, 4 Drawing Sheets

(56) References Cited

U.S. PATENT DOCUMENTS

| | | |
|---|---|---|
| 10,105,523 B2 | 10/2018 | Roorda |
| 10,479,868 B2 | 11/2019 | Mendelsohn et al. |
| 10,525,248 B2 | 1/2020 | Roorda et al. |
| 10,688,056 B2 | 6/2020 | Roorda |
| 10,792,481 B2 | 10/2020 | Roorda |
| 11,021,576 B2 | 6/2021 | Mendelsohn et al. |
| 2006/0063962 A1* | 3/2006 | Drobnik ............ A61M 37/0069 600/7 |
| 2017/0136224 A1* | 5/2017 | Roorda ............. A61M 39/0208 |
| 2019/0091140 A1 | 3/2019 | Mendelsohn et al. |
| 2019/0217070 A1 | 7/2019 | Eversull et al. |
| 2020/0139099 A1 | 5/2020 | Roorda et al. |
| 2020/0330394 A1 | 10/2020 | Roorda |

* cited by examiner

IMPLANT DELIVERY SYSTEM WITH HYDRATION PROMOTOR CAPABILITY

CROSS-REFERENCES TO RELATED APPLICATIONS

This application is a continuation of PCT/US2017/054897, filed Oct. 3, 2017, which claims the benefit of U.S. Provisional Patent Application No. 62/404,027, filed Oct. 4, 2016, the teachings of which are hereby incorporated by reference in its entirety for all purposes.

BACKGROUND OF THE INVENTION

Many beneficial substances, including many therapeutic agents, require long-term delivery to a target site of action to be optimally effective. Well-known examples include drugs that need to be administered for extended periods of time to a patient. Many extended release formulations have been developed for this purpose. A common issue with all of these formulations is that the drugs administered need to be stabilized in the formulation for the duration of the shelf-life of their dosage form, in addition to the stabilization required during the extended release period.

In many cases, drugs are more stable in a dry or solid formulation than in a dissolved state, hence formulations having a solid formulation during shelf life are often preferred. In some instances, the solid drug may be dispersed in a liquid, resulting in a liquid formulation comprising a solid drug. However, in order to be released from their dosage form, drugs almost always rely on some type of diffusional mechanism, which inherently requires the drugs to be in solution. Therefore, many dosage forms rely on the uptake of water after administration to a patient to bring the drugs from a solid form into solution, prior to release from the dosage form.

One type of dosage form that has been developed to address the issue of extended release of therapeutic agents is that of implantable drug delivery devices, in which a reservoir holding a drug formulation is combined with a release rate controlling mechanism, such as a release rate controlling membrane. In many instances, when a solid or dry formulation, like a powder, is filled into such a reservoir, a quantity of air is included in the reservoir. As was mentioned above, many of these dosage forms rely on the uptake of water to bring their drugs from the solid form into solution, essentially requiring that air inside the reservoir be replaced with water. Oftentimes, this will require simultaneous mass transport of water into a device and air out of the device. For those dosage forms that do not allow for such simultaneous transport, proper hydration of the formulation inside the reservoir may be impeded. One type of dosage form where this can be the case is implantable drug delivery systems having a capsule encapsulating a reservoir containing a therapeutic agent in a dry form, and a release rate controlling membrane based on nanopores. In many cases, the reservoir and the nanopores will contain an amount of air in addition to the therapeutic agent, and mass transport of interstitial fluid into the reservoir after implantation may be impeded by the presence of the air. Therefore, additional technologies are desired that allow for proper hydration in such dosage forms.

BRIEF SUMMARY OF THE INVENTION

In one embodiment, the present invention provides an apparatus for promoting fluid uptake into an implantable drug delivery device, the apparatus comprising:
a housing;
a tubular outer member, extending from the housing in a distal direction and having a lumen;
an obturator, at least partially slideably disposed within the lumen of the tubular outer member;
a pressure reducer; and
a connector for transport of fluids, the connector being in fluid contact with the lumen of the tubular outer member.

In certain aspects, the connector is connected with the housing.

In certain aspects, the connector is connected with the tubular outer member.

In certain aspects, the apparatus further comprises:
a removable sealing means forming a hermetic seal with the distal end of the outer member, wherein the connector is connected with the sealing means.

In certain aspects, the sealing means is one of a cap and a plug.

In certain aspects, the connector is a valved connector.

In certain aspects, the connector is a 3-way connector.

In another embodiment, the present invention provides an apparatus for promoting fluid uptake into an implantable drug delivery device, the apparatus comprising:
a housing;
a tubular outer member, extending from the housing in a distal direction and having a lumen;
an obturator, at least partially slideably disposed within the lumen of the tubular outer member;
a pressure reducer;
a reservoir containing a biocompatible fluid; and
a connector for transport of fluids, the connector being in fluid contact with the lumen of the tubular outer member and with the reservoir containing the biocompatible fluid.

In another embodiment, the present invention provides an apparatus for promoting fluid uptake into an implantable drug delivery device, the apparatus comprising:
a housing;
a tubular outer member, extending from the housing in a distal direction and having a lumen;
an obturator, at least partially slideably disposed within the lumen of the tubular outer member; and
a connector for transport of fluids, the connector being in fluid contact with the lumen of the tubular outer member.

In certain aspects, the connector is connected with the housing.

In certain aspects, the connector is connected with the tubular

The apparatus as described above, further comprises: a removable sealing means forming a hermetic seal with the distal end of the outer member;

In certain aspects, the sealing means is one of a cap and a plug.

In certain aspects, the connector is a valved connector.

In certain aspects, the connector is a 3-way connector.

In yet another embodiment, the present invention provides a method for promoting fluid uptake into an implantable drug delivery device, the device having a reservoir and a nanoporous membrane in fluid contact with the reservoir, the method comprising:

providing an apparatus, comprising:

a housing;

a tubular outer member, extending from the housing in a distal direction and having a lumen;

an obturator, at least partially slideably disposed within the lumen of the tubular outer member;

a pressure reducer; and a connector for transport of fluids, the connector being in fluid contact with the lumen of the tubular outer member;

providing the implantable drug delivery device in a location within the lumen of the tubular outer member;

operating the pressure reducer to reduce pressure in the reservoir of the drug delivery device;

connecting a reservoir containing a biocompatible fluid with the connector;

admitting biocompatible fluid through the connector into the lumen of the outer member, and allowing biocompatible fluid to enter the reservoir through the nanoporous membrane.

In certain aspects, the method further comprises the steps of:

inserting the outer member into an anatomically suitable location in a subject; and depositing the implantable drug delivery device and a quantity of the biocompatible fluid in the anatomically suitable location.

In another embodiment, the present invention provides a method for promoting fluid uptake into an implantable drug delivery device, the device having a reservoir and a nanoporous membrane in fluid contact with the reservoir, the method comprising:

providing an apparatus, comprising:

a housing;

a tubular outer member, extending from the housing in a distal direction and having a lumen;

an obturator, at least partially slideably disposed within the lumen of the tubular outer member;

a pressure reducer;

a reservoir containing a biocompatible fluid; and a connector for transport of fluids, the connector being in fluid contact with the lumen of the tubular outer member and with the reservoir containing the biocompatible fluid;

providing the implantable drug delivery in a location within the lumen of the tubular outer member;

operating the pressure reducer to reduce pressure in the reservoir of the drug delivery device;

admitting biocompatible fluid through the connector into the lumen of the outer member; and allowing biocompatible fluid to enter the reservoir through the nanoporous membrane.

In certain aspects, the method further comprises the steps of:

inserting the outer member into an anatomically suitable location in a subject; and depositing the implantable drug delivery device and a quantity of the biocompatible fluid in the anatomically suitable location.

In still yet another embodiment, the present invention provides a method for promoting fluid uptake into an implantable drug delivery device, the device having a reservoir and a nanoporous membrane in fluid contact with the reservoir, the method comprising:

providing an apparatus, comprising:

a housing;

a tubular outer member, extending from the housing in a distal direction and having a lumen;

an obturator, at least partially slideably disposed within the lumen of the tubular outer member; and a connector for transport of fluids, the connector being in fluid contact with the lumen of the tubular outer member;

providing the implantable drug delivery in a location within the lumen of the tubular outer member;

connecting a pressure reducer with the connector and reducing pressure in the reservoir of the drug delivery device;

admitting a biocompatible fluid into the lumen of the outer member, and allowing biocompatible fluid to enter the reservoir through the nanoporous membrane.

In certain aspects, the method further comprises the steps of:

inserting the outer member into an anatomically suitable location in a subject; and depositing the implantable drug delivery device and a quantity of the biocompatible fluid in the anatomically suitable location.

These and other aspects, objects and embodiments will become more apparent when read with the detailed description of the invention and the figures which follow.

DETAILED DESCRIPTION OF THE INVENTION

I. Definitions

Figure 1A:
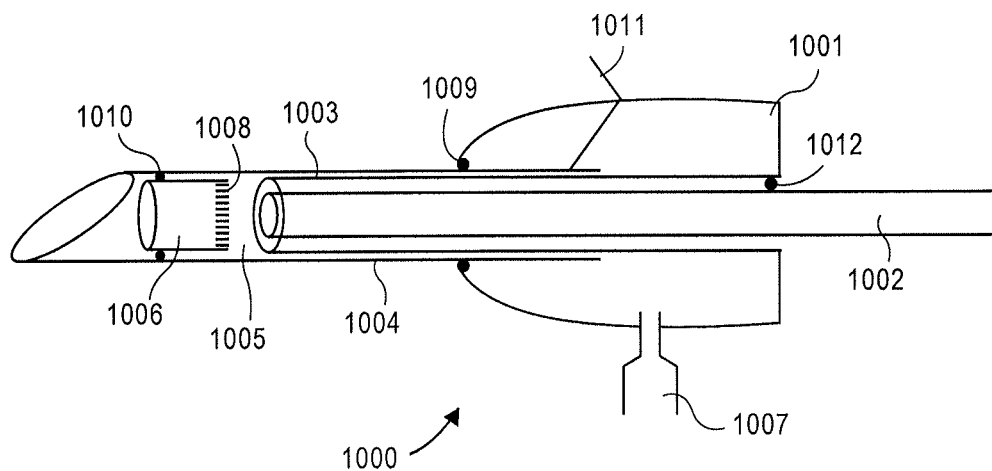
FIG. 1A illustrates an embodiment of the invention with a connector attached to a housing.

"Obturator" includes an elongated member, suitable for moving an object within a tubular member with respect to the tubular member.

"Membrane" includes a porous structure allowing mass transport of molecules from one side of the structure to the other through the structure.

"Porous membrane" includes a porous structure wherein at least some of its pores are open on both ends and form fluid-filled pathways allowing for mass transport through the structure by fluid flow.

"Nanoporous membrane" includes a porous structure wherein at least some of its pores are open on both ends and form fluid-filled pathways having a smallest dimension less than one micrometer and allowing for mass transport through the structure by fluid flow.

"Titania nanotube membrane" includes a nanoporous membrane having an array of titania nanotubes on a titanium substrate where at least a portion of the titania nanotubes are open at both ends and capable of allowing mass transport from one side of the membrane to the other through the titania nanotubes by fluid flow.

"Polypeptide," "peptide," and "protein" are used interchangeably herein to include a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins, wherein the amino acid residues are linked by covalent peptide bonds.

"Fluid contact" includes a location of two or more entities relative to each other in a manner that allows for fluid-phase mass transport between the entities.

"Water-soluble gas" includes a gas that has a solubility in water at a temperature of 37° C. and a pressure of 1 atmosphere that is greater than the solubility of air in water at a temperature of 37° C. and a pressure of 1 atmosphere. The equilibrium solubility of air (oxygen and nitrogen combined) in water under these conditions is about 22 mg/liter (22 µg/mL). A water soluble gas (or mixture of gases) has a solubility of more than 22 mg/liter such as 23, 24, 25, 26, 27, 28, 29, 30, 31, 32, 33, 34, 35, 36, 37, 38, 39, 40 or more than 40 mg/liter.

The term "distal" in reference to a medical device or part thereof generally includes an orientation away from a medical user of the device and towards a subject or patient. The term "proximal" in reference to a medical device or part thereof generally refers to an orientation towards a medical user of the device and away from a subject or patient.

The term "biodegradable" includes the ability of a polymeric substance to degrade into lower molecular weight species when introduced into a biological environment. Examples include biodegradable polymers such as poly (lactic-co-glycolic acid) (PLGA).

The term "soluble" includes the ability of a substance to dissolve into a solvent such as a biological fluid, without degrading into lower molecular weight species. Examples include biocompatible polymers like polyethylene glycol and polyvinyl pyrrolidone.

II. Embodiments

In certain aspects, the present invention pertains to the field of implantable drug delivery devices having a reservoir containing a therapeutic agent, and having one or more membranes providing pathways for mass transport through fluid flow between the reservoir and an environment of the drug delivery device. In preferred embodiments the membranes are porous membranes. The membranes may be configured to provide sustained release of the therapeutic agent after implantation of the device in the body of a subject. In some embodiments the membrane is a microporous membrane. In some embodiments the membrane is a nanoporous membrane such as those described in U.S. Patent Application Pub. No. 2014/0371687, incorporated herein by reference.

For shelf-stability purposes (i.e., shelf-life), it is often preferred that the therapeutic agent in such devices is in a solid state during storage of the device. In order for release of the therapeutic agent to occur, fluid may need to be introduced into the reservoir to dissolve the therapeutic agent and enable its release through the porous membrane.

Embodiments of the invention include apparatuses and methods to promote uptake of fluids into the reservoir of an implantable drug delivery device. In some embodiments a drug delivery device is part of the embodiment. In certain instances, the apparatuses, methods and means enable fluid uptake into a drug delivery device having a reservoir, wherein the reservoir has a pressure which is less than atmospheric pressure (sub-atmospheric i.e., reduced pressure), such as less than 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, less than 0.01 atmosphere (<0.01) or even less. In certain aspects, the reservoir has a pressure of 0.009, 0.008, 0.007, 0.006, 0.005, 0.004, 0.003, 0.002, 0.001 atm or even less. The reduced pressure promotes the uptake of fluid into the reservoir for example, prior to implantation.

Embodiments of the invention promote uptake of fluids into a reservoir of an implantable drug delivery device through a porous membrane by creating a pressure differential between the reservoir in the device and a fluid-filled environment outside the device. Specifically, embodiments of the invention combine the generation of a reduced pressure inside a reservoir of a drug delivery device with supplying a quantity of a biocompatible fluid outside the drug delivery device, the fluid being brought in contact with the membrane. Generation of a pressure differential between the reservoir inside the device and the biocompatible liquid outside the device, combined with the capability of the membrane to provide mass transport through fluid flow, promotes uptake of the biocompatible fluid through the membrane into the reservoir of the device.

Some embodiments of the invention are suitable for introducing or implanting the drug delivery device into the body of a subject, as well as for promoting in vitro uptake of a biocompatible fluid into the reservoir.

In some embodiments of the invention, uptake of a biocompatible fluid into the reservoir of the drug delivery system may be completed inside an apparatus used to create the pressure differential and to provide the biocompatible fluid.

In some embodiments of the invention, uptake of a biocompatible fluid may be initiated inside an apparatus used to create the pressure differential and to provide the biocompatible fluid, after which the partially fluid-filled drug delivery device may be inserted together with a quantity of the biocompatible fluid into a subject to be treated, for instance in a subcutaneous pocket, to allow the uptake of the biocompatible liquid to go to completion.

The extent to which uptake of fluids into the drug delivery device can be accelerated may depend on the particular design of the device, on the amount of residual void volume in the reservoir of the device to be filled, on the viscosity of the biocompatible fluid, on the permeability of the membrane, on the pressure gradient, etc. Some embodiments of the invention are capable of exerting additional pressure on the biocompatible fluid in contact with the membrane to accelerate fluid uptake even more.

For instance, a device has an internal volume of 20 µL, and is 90% filled with solid drug, leaving a residual void volume of 2 µL. It has a membrane with a permeability for a biocompatible fluid, in this case Phosphate Buffered Saline (PBS), of 0.5 µL/(min.Atm). The minimum pressure that can be created and maintained in a reservoir of a drug delivery device in contact with a PBS may be the vapor pressure of PBS, which, at room temperature is about 0.022 Atm. As a result, evacuation of the device and bringing the membrane in contact with PBS at ambient conditions may create a pressure differential of close to 1 atmosphere. In this case, (and assuming that the void space is mostly filled with water vapor containing a negligible amount of residual air) complete filling of the void volume may take about 4 minutes or less, such as 3, 2, or 1 minute. A fill time like this may be suitable to perform a complete filling procedure inside an apparatus according to the invention in a physician's office.

By contrast, an alternative drug delivery device has a residual void volume of 1 µL, and a membrane with a permeability of 0.1 µL/(min.Atm), leading to a time of 100 minutes to fill. This may be prohibitively long to perform in a doctor's office. In this case, the hydration may be started in the apparatus, after which the device and a quantity of biocompatible liquid may be inserted into a subcutaneous skin pocket to complete filling.

Some embodiments of the invention comprise a housing. Functions of the housing may include holding other components of the invention together into an apparatus suitable for use, providing a handle for an user to hold and operate the apparatus, and the like. The housing may be constructed out of any suitable material, including polymers, ceramics, composites and combinations thereof. Oftentimes, for purposes of ease of manufacturing and cost reduction, the housing will comprise molded polymeric parts.

Some embodiments of the invention comprise a tubular outer member having a lumen, such as a tubular insertion member or tubular implantation member, extending from the housing in a distal direction. In some embodiments the outer member is attached to the housing. In some embodiments, the outer member is a slideable member, at least partially slideably disposed within the housing. The outer member may be configured to hold an implantable drug delivery device. In some embodiments the insertion member or implantation member is a sharpened member, such as a hollow needle, suitable to penetrate the skin, to access areas within the body of a subject, such as the subcutaneous space, and deliver an implantable drug delivery device into the subcutaneous space. In some embodiments the tubular insertion member is a blunt member, suitable to access areas within the body of a subject after penetrating the skin with a separate implement, such as a scalpel. In some embodiments the separate implement is included in the embodiment. The tubular outer member may be constructed out of any suitable material. Preferred materials of construction include metals, polymers, ceramics, composites and combinations thereof. Examples of metals include stainless steel and titanium. Examples of polymers include polyethylene, polypropylene, polyurethanes, acrylonitrile butadiene styrene, polyether ether ketone, etc.

Some embodiments comprise an obturator. Obturators of the invention may comprise elongated members, slideably disposed within a tubular outer member. In some embodiments the obturators are slideable obturators. In some embodiments, the obturators are attached to the housing, and the tubular outer member is slideable disposed around the obturator. Functions of the obturator include providing a means to an operator to move an implantable drug delivery device, disposed within the tubular outer member, with respect to the tubular outer member or to hold a drug delivery device, disposed within a tubular outer member stationary, while moving the tubular outer member. The obturator may be constructed out of any suitable material. Preferred materials of construction include metals, polymers, ceramics, composites and combinations thereof. Examples of metals include stainless steel and titanium. Examples of polymers include polyethylene, polypropylene, polyurethanes, acrylonitrile butadiene styrene, polyether ether ketone, etc.

Some embodiments of the invention comprise a pressure reducer. In embodiments comprising a drug delivery device, the pressure reducer may be in fluid contact with the membrane of the drug delivery device. Some embodiments comprise a pressure reducer configured as a slideable elongated member. In some embodiments the pressure reducer is at least partially slideably disposed within the outer member. In some embodiments the obturator is a tubular obturator, and the pressure reducer is at least partially slideably disposed within the obturator. In some embodiments, the pressure reducer is a tubular pressure reducer, and the obturator is at least partially slideably disposed within the pressure reducer. In some embodiments, the obturator and the pressure reducer are at least partially slideably disposed within the outer member in a side-by-side configuration.

Some embodiments comprise a slideable pressure reducer outside the tubular outer member, for instance in a cavity in a housing, wherein the housing holds the outer member, the obturator and the pressure reducer.

Functions of the pressure reducer include providing a means to an operator to reduce the pressure inside a reservoir of an implantable drug delivery system to promote uptake of fluids into the reservoir.

In some embodiments, operating the pressure reducer reduces the pressure inside the tubular outer member or inside the cavity in the housing to less than 0.5 atmosphere. In preferred embodiments the pressure is reduced to less than 0.1 atmosphere. In most preferred embodiments, the pressure is reduced to less than 0.01 atmosphere.

The pressure reducer may be constructed out of any suitable material. Preferred materials of construction include metals, polymers, ceramics, composites and combinations thereof. Examples of metals include stainless steel and titanium. Examples of polymers include polyethylene, polypropylene, polyurethanes, acrylonitrile butadiene styrene, polyether ether ketone, etc.

Some embodiments include connectors for connecting to a separately supplied pressure reducer, such as a syringe or a vacuum pump.

Some embodiments of the invention include a connector in fluid contact with the lumen of the outer member, for instance for connecting the lumen of the tubular outer member to other components of the embodiment, such as a reservoir with a biocompatible fluid or a pressure reducer. The connector may be any type of connector suitable for transport of fluids, including Luer type connectors, such as a Luer slip or Luer lock connectors. In preferred embodiments the connector is 2-way connector, connecting the lumen to a single other component, or a 3-way connector, connecting the lumen to two other components. Higher numbers of connections are possible within the scope if the invention.

In some embodiments the connector is a valved connector. In some embodiments the connector is a sealed connector with a breakable seal, that can be broken by connecting the connector to an outside source of fluid, such as a reservoir containing a biocompatible liquid.

In some embodiments the connector is an open connector, and control over the connection is obtained by other means, such as a valve on the reservoir with the biocompatible liquid, rather than on the connector.

Preferred materials of construction include metals, polymers, ceramics, composites and combinations thereof. Examples of metals include stainless steel and titanium. Examples of polymers include polyethylene, polypropylene, polyurethanes, acrylonitrile butadiene styrene, polyether ether ketone, etc.

Some embodiments of the invention include an implantable drug delivery device, slideably disposed within the tubular outer member. Drug delivery devices useable in the current invention comprise at least one reservoir containing a formulation of a therapeutic agent to be delivered from the device. Drug delivery devices of the invention further comprise at least one membrane to provide a pathway for delivery of the therapeutic agent out of the reservoir of the device and into an environment of use. In preferred embodiments the membrane is configured to control the release of the therapeutic agent for extended periods of time. In some preferred embodiments, release of the beneficial substance(s) is extended over at least one month. In more preferred embodiments, the release is extended over at least three months, 4, 5, 6, 7, 8, 9, 10, 11, or at least 12 months.

In some embodiments, a membrane controlling the rate of release of the therapeutic agent is a nanoporous membrane. In certain embodiments, there are two or more membranes in the device.

In some embodiments, the pores in the membranes are nanochannels, such as those disclosed in U.S. Pat. No. 8,480,637 incorporated herein by reference. In some embodiments, the pores in the membranes are nanotubes, such as those disclosed in U.S. Patent Application Pub. No. 2014/0371687 incorporated herein by reference.

In some embodiments, compositions of the invention are disposed within a reservoir of an extended-release dosage form controlled by a nanoporous membrane, wherein the nanoporous membrane is configured to achieve extended-release of the therapeutic agent from the reservoir of a device. In some embodiments, the release rate of the therapeutic agent is controlled by matching the dimensions of the pores in the nanoporous membrane to the molecular dimensions or the hydrodynamic dimensions of the therapeutic agent. In some embodiments, the smallest dimension of the pores is not more than 5 times a molecular dimension or hydrodynamic dimension of the therapeutic agent. In some embodiments, the smallest diameter of the pores is not more than 1, 2, 3, 4, 5, 6, 7, 8, 9, 10, 11, or 12 times a molecular dimension or hydrodynamic dimension of the therapeutic agent.

The drug delivery device may be held in place by any desired means, including means such as a precision fit inside the outer member with tolerances to provide adequate immobilization of the device or an adequate sealing function as described below, while still allowing for sufficient slideability of the device. In some embodiments the device or the outer member may have a slightly ovalized section to provide a friction fit to hold the device in place. Some embodiments of the invention include a separate drug delivery device, configured to be loaded into a tubular outer member prior to use. Some embodiments of the invention do not include a drug delivery device, and are configured to be loaded with a separately provided drug delivery device.

In some embodiments the drug delivery device contains a formulation of protein or peptide. Suitable peptides include, but are not limited to, beta-glucocerobrosidase, interferon alpha, interferon beta, interferon gamma, agasidase alpha, agasidase beta, exenatide, octreotide, LHRH, LHRH analogs, calcitonin, nutropin/somatropin, factor VIII, aldesleukin, forigerimod, NP fusion proteins, IL-12, a melanocyte stimulating hormone, and bapineuzumab. In some embodiments, the protein or peptide therapeutic agents are Glucagon-Like Peptide-1 receptor agonists also known as GLP-1 receptor agonists. In some embodiments, the GLP-1 receptor agonist is exenatide. In certain instances, exenatide has CAS No. 141732-76-5 and an empirical formula of $C_{184}H_{282}N_{50}O_{60}S$. In preferred embodiments, the amount of exenatide can be from about 60 µg to about 50 mg, such as 100 µg, 200 µg, 300 µg, 400 µg, 500 µg, 600 µg, 700 µg, 800 µg, 900 µg, 1 mg, 10 mg, 20 mg, 30 mg, 40 mg, or 50 mg.

FIGS. 1A-1D illustrate, schematically, the structure and function of a number of components of embodiments of the invention. Implanter 1000 has housing 1001, which serves as an attachment component for several other parts of the implanter, and as a handle for a medical professional to operate the device.

Obturator 1003 is attached to housing 1001. Pressure reducer 1002 is slideably disposed within obturator 1003. O-ring 1012 provides a sliding hermetic seal between obturator 10003 and pressure reducer 1002. Tubular outer member 1004 is slideably disposed within housing 1001, and around obturator 1003. Implantable drug delivery device 1006 with membrane 1008 is slideably disposed within lumen 1005 of outer member 1004.

Retraction mechanism 1011 provides a means to retract outer member 1004 from a subcutaneous pocket during use of the device, while housing 1001 and attached obturator 1003 are held stationary, this effectively expelling drug delivery device 1006 from the outer member.

In FIG. 1A, connector 1007 is connected with housing 1001, and is in fluid contact with lumen 1005 and membrane 1008. In this exemplary embodiment a fluid path through housing 1001 is provided in order to provide a fluid contact path between connector 1007 and lumen 1005. For example, housing 1001 may contain a channel for that purpose, or may be hollow. In order to maintain reduced pressure inside housing 1001, O-ring 1009 provides a sliding, hermetic seal between housing 1001 and slideable outer member 1004. In order to maintain reduced pressure in outer member 1004, a cap may be provided at the distal end of outer member 1004, or, as illustrated in FIG. 1A, O-ring 1010 may be used to provide a sliding hermetic seal between drug delivery device 1006 and outer member 1004.

During operation of implanter 1000, a user can move pressure reducer 1002 in a proximal direction, reducing pressure in lumen 1005, and inside the reservoir of drug delivery device 1006. Next, a biocompatible liquid can be admitted through connector 1007 into lumen 1005, and into contact with membrane 1008. After a hydration period to be determined by the user, the drug delivery device can be implanted under the skin of a patient, together with the desired amount of the biocompatible fluid. Connector 1007 may connect to an external reservoir, fluid supply or an accessory unit suitable for improving fluid uptake into the lumen 1005.

Figure 1B:
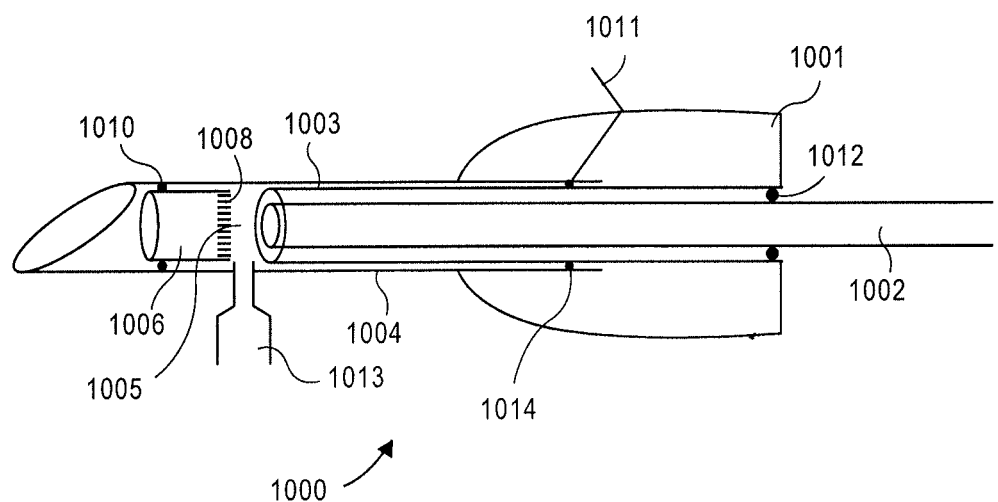
FIG. 1B illustrates an embodiment of the invention with a connector attached to a tubular outer member.

In FIG. 1B, connector 1013 is connected with tubular outer member 1004, and is in fluid contact with lumen 1005 and membrane 1008. In order to maintain reduced pressure in outer member 1004, a cap may be provided at the distal end of outer member 1004, or, as illustrated in FIG. 1B, O-ring 1010 may be used to provide a sliding hermetic seal between drug delivery device 1006 and outer member 1004. In addition, O-ring 1014 provides a sliding hermetic seal between obturator 1003 and outer member 1004. Operation of the device is analogous to what was described in FIG. 1A.

Connector 1013 may connect to an external reservoir, fluid supply or an accessory unit suitable for improving fluid uptake into the lumen 1005.

Figure 1C:
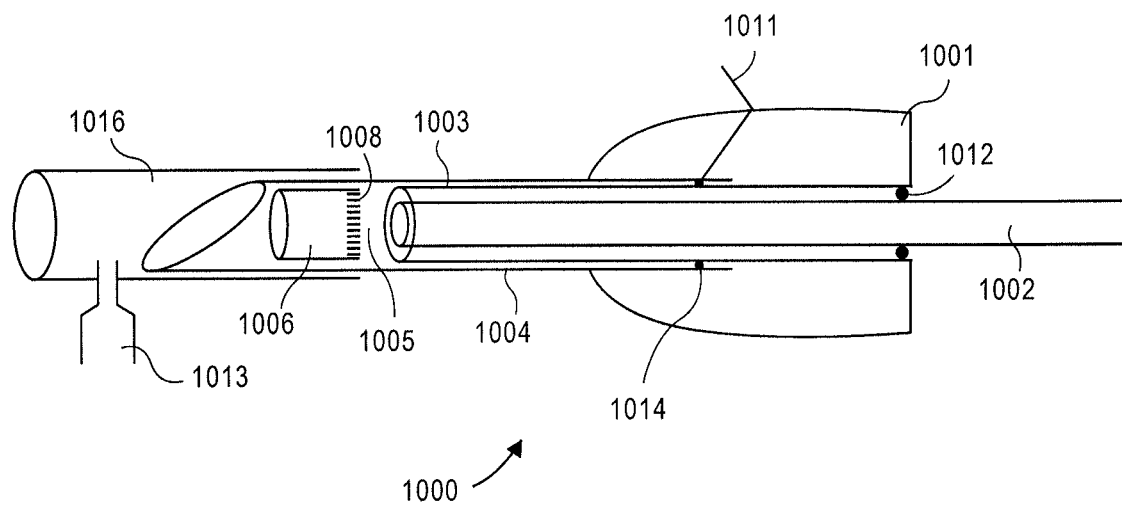
FIG. 1C illustrates an embodiment of the invention with a connector attached to cap over aa tubular outer member.

In FIG. 1C, connector 1013 is connected with cap 1016, which forms a removable sealing means, sealing hermetically over outer member 1004, and is in fluid contact with lumen 1005 and membrane 1008. O-ring 1010, which is shown in FIGS. 1A and 1B, is not present in this embodiment. Implantable drug delivery device 1006 may be located inside lumen 1005 in the orientation as shown, or may be reversed with the membrane facing in a distal direction. Operation of the device is analogous to what was described in FIG. 1A.

Figure 1D:
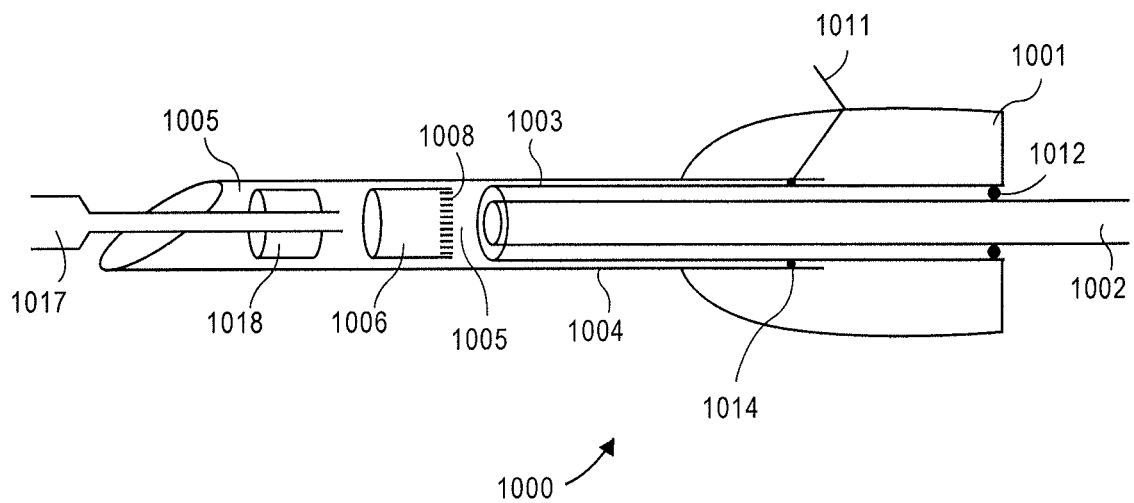
FIG. 1D illustrates an embodiment of the invention with a connector attached to a plug in tubular outer member.

In FIG. 1D, connector 1017 is connected with plug 1018, which forms a removable sealing means, sealing hermetically into outer member 1004, and is in fluid contact with lumen 1005 and membrane 1008. O-ring 1010, which is shown in FIGS. 1A and 1B, is not present in this embodiment. Implantable drug delivery device 1006 may be located inside lumen 1005 in the orientation as shown, or may be reversed with the membrane facing in a distal direction. Operation of the device is analogous to what was described in FIG. 1A.

Figure 2:
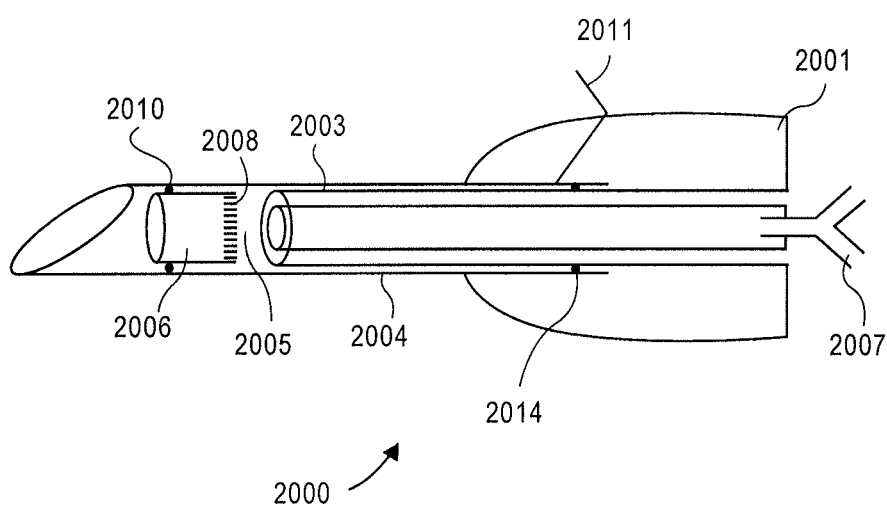
FIG. 2 illustrates an embodiment of the invention without an internal pressure reducer, and with a connector attached to a hollow obturator.

FIG. 2 illustrates a different type of embodiment, wherein the pressure reducer is external to the implanter. Implanter 2000 has housing 2001, which serves as an attachment component for several other parts of the implanter, and as a handle for a medical professional to operate the device.

Obturator 2003 is attached to housing 2001. Tubular outer member 2004 is slideably disposed within housing 2001, and around obturator 2003. Implantable drug delivery device 2006 with membrane 2008 is slideably disposed within lumen 2005 of outer member 2004.

Retraction mechanism 2011 provides a means to retract outer member 2004 from a subcutaneous pocket during use of the device, while housing 2001 and attached obturator 2003 are held stationary, this effectively expelling drug delivery device 2006 from the outer member. O-ring 2010 may be used to provide a sliding hermetic seal between drug delivery device 2006 and outer member 2004. In addition, O-ring 2014 provides a sliding hermetic seal between obturator 2003 and outer member 2004. Obturator 2003 is a hollow obturator 3-way connector 2007 is connected with obturator 2003. Connector 2007 may include a 3-way valve, or, alternatively, valve control may be introduced by valves external to 3-way valve 2007. Connector 2007 may connect to an external reservoir, fluid supply or an accessory unit suitable for improving fluid uptake into the lumen 2005.

During operation of implanter 2000, a user can use an external pressure reducer to reduce pressure in lumen 2005 through one arm of 3-way connector 2007. Next, a biocompatible liquid can be admitted through the other arm of 3-way connector 2007, through hollow obturator 2003, into lumen 2005, and into contact with membrane 2008. After a hydration period to be determined by the user, the drug delivery device can be implanted under the skin of a patient, together with the desired amount of the biocompatible fluid.

Figure 3A:
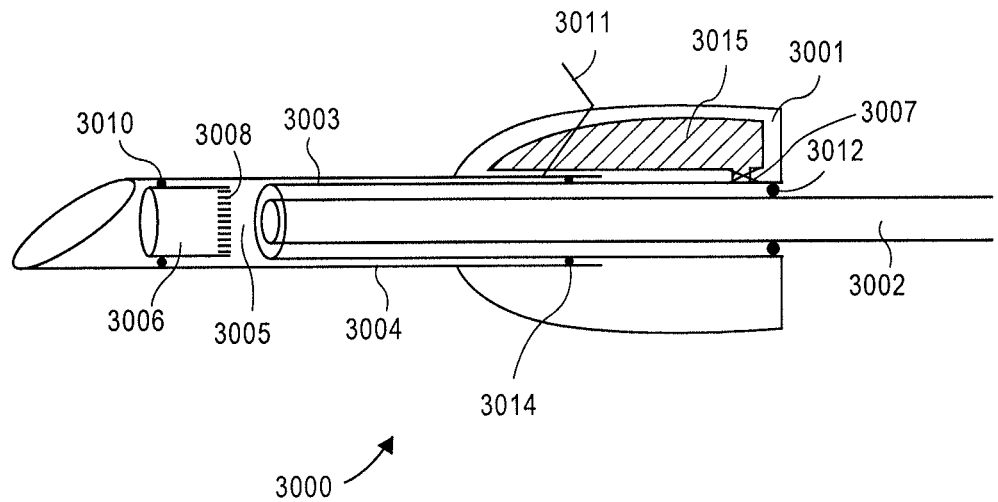
FIG. 3A illustrates an embodiment of the invention with a reservoir containing a biocompatible liquid in the housing, before the step of pressure reduction.

FIGS. 3A and B illustrate an embodiment of the invention including a reservoir containing a biocompatible fluid located inside the housing. In FIG. 3A connector 3007 is located internally in housing 3001, and connects reservoir 3015 with hollow obturator 3003. Reservoir 3015 contains a biocompatible fluid, and may be of a collapsible construction. Hollow obturator 3003 provides a fluid path to lumen 3005 of tubular outer member 3004, to drug delivery device 3006 and to membrane 3008. In FIG. 3A, connector 3007 is a valved connector, and is in a closed position.

Figure 3B:
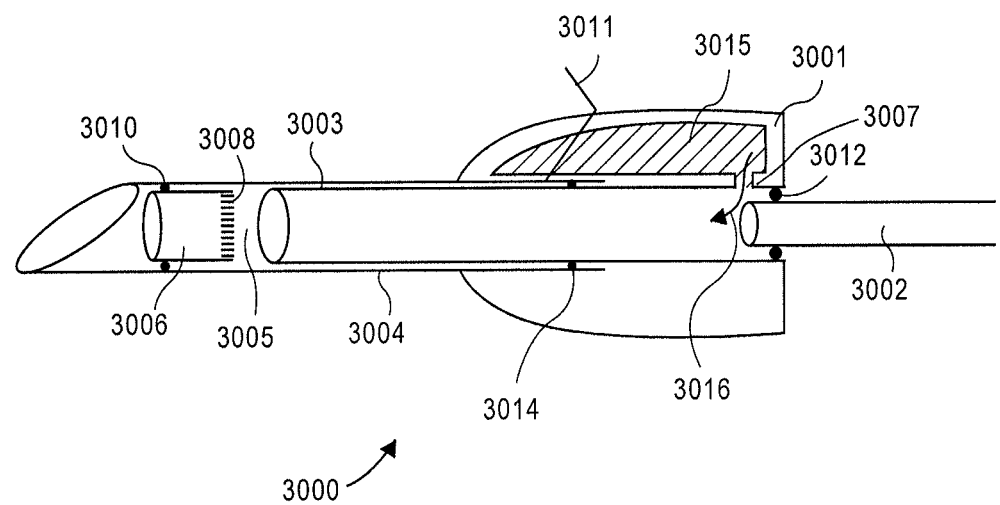
FIG. 3B illustrates an embodiment of the invention with a reservoir containing a biocompatible liquid in the housing, after the step of pressure reduction.

FIG. 3B shows the embodiment after pressure reducer 3002 has been moved in a proximal direction, creating reduced pressure inside hollow obturator 3003, lumen 3005 and inside the reservoir of drug delivery device 3006. Valved connector 3007 has been switched to an open position, and biocompatible fluid is allowed to enter hollow obturator 3003, lumen 3005 and the reservoir of drug delivery device 3006 in the direction of arrow 3016.

It should be understood that the concept of a 3-way connector and an external pressure reducer can be applied to all embodiments shown in FIGS. 1A-1D above.

In some embodiments of the invention, components of the embodiment may be provided as a kit. For instance, the embodiments illustrated in FIG. 1A-1D may be provided with a separate reservoir containing a biocompatible fluid, wherein the reservoir is packaged together with the implanter as a kit.

Incorporated herein by reference, in their entirety and for all purposes are United States Patent Application Pub. No. 2016/0220496, United States Patent Application Pub. No. 2014/0371687, United States Patent Application Pub. No. 2016/0220796, WIPO Patent Application WO/2016/070117, WIPO Patent Application WO/2016/094228, and WIPO Patent Application WO/2016/12302.

It should also understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An apparatus for promoting fluid uptake into an implantable drug delivery device, the apparatus comprising:
   a housing;
   a tubular outer member, extending from the housing in a distal direction and having a lumen;
   an obturator, which is at least partially slideably disposed within the lumen of the tubular outer member;
   a pressure reducer, which is slideably disposed within the obturator; and
   a connector for transport of fluids, the connector being in fluid contact with the lumen of the tubular outer member.

2. The apparatus of claim 1, wherein the connector is connected to the housing.

3. The apparatus of claim 1, wherein the connector is connected with the tubular outer member.

4. The apparatus of claim 1, further comprising:
   a removable sealing means forming a hermetic seal with the distal end of the outer member; and wherein the connector is connected with the sealing means.

5. The apparatus of claim 4, wherein the sealing means is one of a cap and a plug.

6. The apparatus of claim 1, wherein the connector is a valved connector.

7. The apparatus of claim 1, wherein the connector is a 3-way connector.

8. An apparatus for promoting fluid uptake into an implantable drug delivery device, the apparatus comprising:
   a housing;
   a tubular outer member, extending from the housing in a distal direction and having a lumen;
   an obturator, which is at least partially slideably disposed within the lumen of the tubular outer member;
   a pressure reducer, which is slideably disposed within the obturator;

a connector for transport of fluids, the connector being in fluid contact with the lumen of the tubular outer member; and an implantable drug delivery device in a location within the lumen of the tubular outer member.

9. The apparatus of claim 8, wherein the connector is connected with the housing.

10. The apparatus of claim 9, wherein the connector is a valved connector.

11. The apparatus of claim 9, wherein the connector is a 3-way connector.

12. The apparatus of claim 8, wherein the connector is connected with the tubular outer member.

13. The apparatus of claim 8, further comprising:

a removable sealing means forming a hermetic seal with the distal end of the outer member, wherein the connector is connected with the sealing means.

14. The apparatus of claim 13, wherein the sealing means is one of a cap and a plug.

15. A method for promoting fluid uptake into an implantable drug delivery device, the implantable drug delivery device having a reservoir and a nanoporous membrane in fluid contact with the implantable drug delivery reservoir, the method comprising:

providing an apparatus, comprising:

a housing;

a tubular outer member, extending from the housing in a distal direction and having a lumen;

an obturator, which is at least partially slideably disposed within the lumen of the tubular outer member;

a pressure reducer; and a connector for transport of fluids, the connector being in fluid contact with the lumen of the tubular outer member;

providing the implantable drug delivery device in a location within the lumen of the tubular outer member;

operating the pressure reducer to reduce pressure in the implantable drug delivery reservoir of the drug delivery device;

connecting an external reservoir containing a biocompatible fluid with the connector;

admitting the biocompatible fluid through the connector into the lumen of the outer member; and allowing the biocompatible fluid to enter the implantable drug delivery reservoir through the nanoporous membrane.

16. The method of claim 15, further comprising the steps of:

inserting the outer member into an anatomically suitable location in a subject; and depositing the implantable drug delivery device and a quantity of the biocompatible fluid in the anatomically suitable location.

* * * * *